United States Patent [19]

Crose

[11] Patent Number: 5,137,528
[45] Date of Patent: Aug. 11, 1992

[54] AMPOULE FOR ADMINISTERING A LIQUID LOCAL ANAESTHETIC

[76] Inventor: Virginia W. Crose, 7295 Hunt Club Rd., Zionsville, Ind. 46077

[21] Appl. No.: 618,667

[22] Filed: Nov. 26, 1990

[51] Int. Cl.$^5$ .............................................. A61B 19/00
[52] U.S. Cl. .................... 604/415; 604/416; 604/48; 604/91; 604/191; 604/232; 222/337; 222/80
[58] Field of Search ............... 604/191, 232, 236, 416, 604/90, 91, 187, 218, 89, 200, 201, 4, 8, 49, 51, 52, 56, 82, 403, 415; 222/325, 327 X, 326, 80 X

[56] References Cited

U.S. PATENT DOCUMENTS

| | | | |
|---|---|---|---|
| 2,636,493 | 4/1953 | Lockhart | 604/90 |
| 2,688,966 | 9/1954 | Huber | 604/90 |
| 2,705,956 | 4/1955 | McLaughlin | 604/416 |
| 2,869,543 | 1/1959 | Ratcliff et al. | 604/90 |
| 3,091,240 | 5/1963 | McConnaughey et al. | 604/191 X |
| 3,340,873 | 9/1967 | Solowey | 604/416 X |
| 3,464,414 | 9/1969 | Sponnoble | 604/416 X |
| 3,494,359 | 2/1970 | Zackheim | 604/90 |
| 4,405,317 | 9/1983 | Case | 604/90 |
| 4,464,174 | 8/1984 | Ennis | 604/90 |
| 4,950,237 | 8/1990 | Henault et al. | 604/82 |
| 4,968,299 | 11/1990 | Ahlstrand et al. | 604/90 |

FOREIGN PATENT DOCUMENTS

| | | | |
|---|---|---|---|
| 0076722 | 11/1953 | Denmark | 604/416 |
| 2229374 | 9/1990 | United Kingdom | 604/191 |

*Primary Examiner*—C. Fred Rosenbaum
*Assistant Examiner*—Mark O. Polutta
*Attorney, Agent, or Firm*—Jack Schuman

[57] ABSTRACT

An ampoule is disclosed having a stopper slidably mounted therein adjacent the proximal end and a rubber diaphragm secured to the distal end. An aperture barrier is provided in the ampoule between the proximal and distal ends, and has an aperture sealed by a plug. Sterile acidified liquid local anaesthetic is contained in an proximal compartment defined in the ampoule by the barrier and the stopper. Sterile alkaline neutralizing reagent is contained in the distal compartment defined in the ampoule by the barrier and the rubber diaphragm. In use, the ampoule is placed in the barrel of a hypodermic syringe, and is then manually advanced in the barrel toward the distal end of the syringe to cause the proximal end of the hypodermic needle of the syringe, which proximal end extends into the barrel of the syringe, to perforate the rubber diaphragm and communicate with the distal compartment of the ampoule. The distal end of the hypodermic needle is then inserted into the oral tissues of the patient. Thereafter, the plunger of the hypodermic syringe is advanced against the stopper to advance the stopper in the ampoule, thereby to pressurize the local anaesthetic in the proximal compartment sufficiently to dislodge the plug from the barrier aperture into the distal compartment, and to force the acidified local anaesthetic into the alkaline neutralizing reagent and thence immediately into the tissues of the patient.

3 Claims, 1 Drawing Sheet

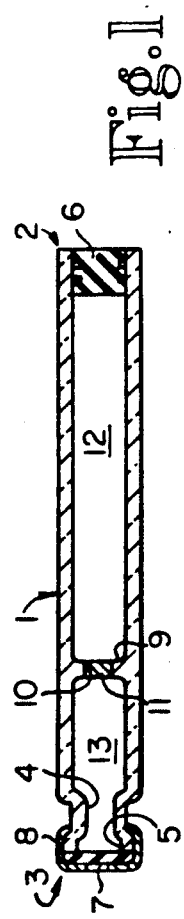
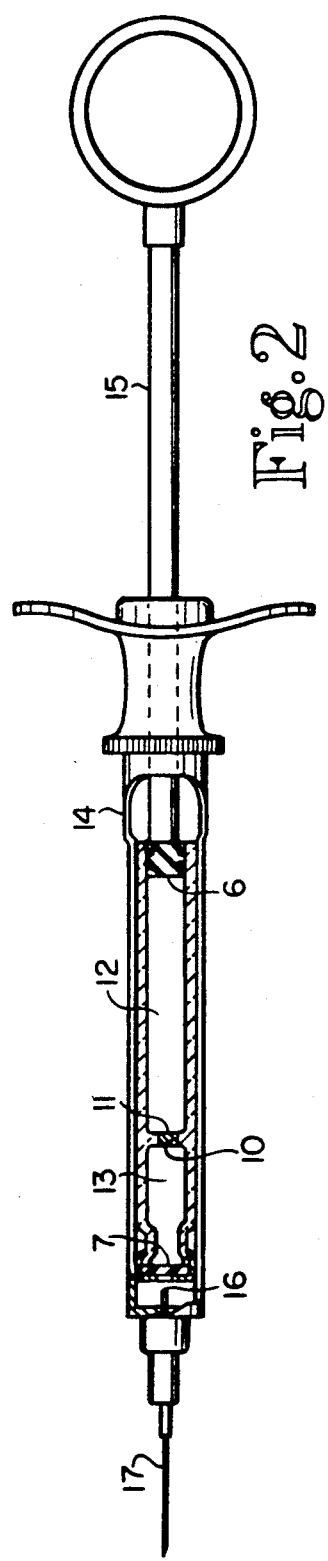
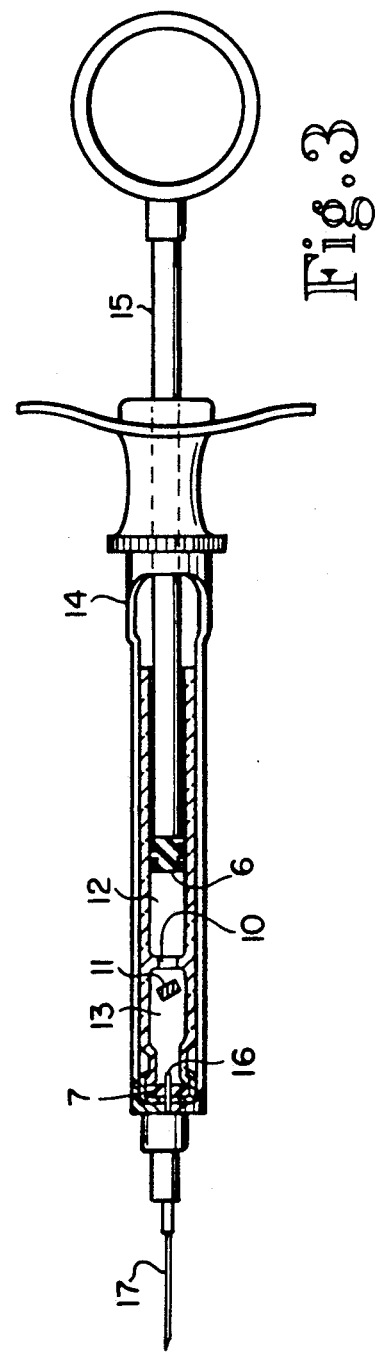

AMPOULE FOR ADMINISTERING A LIQUID LOCAL ANAESTHETIC

BACKGROUND OF THE INVENTION (1) Field of the Invention

This invention relates broadly to a novel ampoule adapted to contain a liquid local anaesthetic and to a novel method for administering such anaesthetic.

More specifically, the apparatus of this invention relates to a novel ampoule adapted to contain an acidified liquid local anaesthetic and adapted to be placed in a standard hypodermic syringe prior to administration of the anaesthetic, which ampoule is compartmented to provide a proximal compartment for the liquid local anaesthetic adjacent the proximal end of the ampoule and a distal compartment for a liquid neutralizing agent adjacent the distal end of the ampoule.

More specifically, the method of this invention relates to the administration of an acidified liquid local anaesthetic through a body of alkaline liquid neutralizing reagent and thence into the tissues of a patient.

(2) Description of the Prior Art

The administration of local anaesthetics is a well-known procedure in the practice of medicine and dentistry.

The administration of a local anaesthetic typically involves the use of an ampoule, which may be of glass, containing the liquid local anaesthetic. The ampoule, immediately prior to use, is placed in the barrel of a conventional hypodermic syringe having a hand-operated plunger at the proximal end thereof and a hollow hypodermic needle at the distal end thereof, the proximal end of the hollow hypodermic needle extending partially into the barrel of the syringe. The proximal end of the ampoule is closed by a rubber stopper slidably fitted within the ampoule. The distal end of the ampoule is closed by a rubber diaphragm. In administering the local anaesthetic, the operator manually advances the ampoule in the barrel toward the distal end of the hypodermic syringe, thereby to cause the proximal end of the hypodermic needle, which extends into the barrel of the syringe, to perforate the rubber diaphragm at the distal end of the ampoule and communicate with the interior of the ampoule. Thereafter, the operator advances the plunger of the syringe against the rubber stopper of the ampoule, forcing the rubber stopper into the ampoule. The rubber stopper functions as a piston, forcing the local anaesthetic out of the distal end of the ampoule, through the hollow hypodermic needle and into the tissues of the patient.

Ampoules of the type described are well-known, one being an ampoule manufactured by Cook-Waite Laboratories, Inc. and sold under their registered trademark CARPULE.

Certain local anaesthetics, particularly used in the practice of dentistry, have relatively short shelf lives if they are alkaline, i.e., having a pH greater than 7.0. If these anaesthetics are acidified, their shelf lives can be increased substantially. Local anaesthetics such as lidocaine and mepivacaine are generally marketed as lidocaine and mepivacaine hydrochloride, respectively, with a pH as low as 5.0, meaning that they are quite acidic, and these acidified local anaesthetics have shelf lives of three to four years.

However, the administration of an acidified local anaesthetic causes a substantial amount of discomfort, and indeed pain, particularly in infiltrative local anaesthesia as employed in dentistry. It is known that very slow infiltration of the acidified local anaesthetic can reduce the pain associated with infiltration. It is a fact of life that demands on a dentist's time may preclude a very slow infiltration of local anaesthetic, especially with children, who frequently are agitated and fearful.

A partial solution to this problem has recently been devised. A sterile hypodermic needle was inserted into one end of an ampoule containing acidified liquid local anaesthetic and a portion of such anaesthetic was removed from the ampoule. A sterile hypodermic needle was then used to inject, through one end of the ampoule, a quantity of alkaline reagent. The quantity of alkaline reagent so injected into the ampoule, and its concentration, were sufficient to bring the pH of the mixture, after the ampoule was shaken to mix the two solutions, to above 7.0. Specifically, 0.18 ml. of anaesthetic solution such a 2% lidocaine hydrochloride (1/10 the volume of a 1.8 ml. ampoule) were replaced with 0.18 ml. of 8.4% sodium bicarbonate. The mixed solution was then administered to 50 patients, only 5 of whom said the injection hurt, only 15 of whom said the injection stung (most saying the sting was very little), 36 of whom said this procedure was more comfortable than previous procedures with acidified local anaesthetic, and 38 of whom reported that the injection was painless or they felt nothing. Clearly, neutralization of acidified local anaesthetic dramatically decreased the pain and discomfort normally associated with infiltration.

This partial solution, while effective, had certain shortcomings. Any time that sterile liquids are removed from an ampoule or injected into an ampoule, there is a risk of contamination, and therefore the partial solution mandated the application of most rigorous measures to assure sterility. Because the acidity of the local anaesthetic was neutralized, its shelf life was markedly reduced, and therefore the mixture of acidified local anaesthetic and neutralizing alkaline reagent could not be made up much in advance of its use.

It is known to provide a glass vial having a necked-down portion intermediate the ends thereof with a rubber stopper seated in the necked-down portion to define a first compartment adapted to contain a liquid and a second compartment adapted to contain a powder. A rubber diaphragm seals the open end of the vial. In use, the rubber diaphragm is pushed inwardly to pressurize the liquid in the first compartment and dislodge the rubber stopper from the necked-down portion of the vial. The vial is then shaken to mix the liquid and the powder so as to dissolve the powder. Thereafter, the needle of a hypodermic syringe is advanced through the rubber diaphragm into the vial and the solution in the vial is withdrawn for subsequent injection into the tissues of a patient. This vial, used by The Upjohn Company of Kalamazoo, Mich., is not an ampoule, does not solve the problems to which the present invention is directed, and does not function as an ampoule, particularly of the type herein disclosed and claimed.

SUMMARY OF THE INVENTION

One of the objects of this invention is to provide an improved ampoule adapted to separately contain two discrete liquids prior to their use.

Another of the objects of this invention is to provide an improved compartmented ampoule adapted to contain discrete liquids separately in said compartments, with means to permit said discrete liquids to mix in the ampoule prior to use.

Yet another object of this invention is to provide an improved method to inject a first liquid into the tissue of a patient through a second liquid which acts on the first liquid to mitigate or eliminate an undesirable characteristic of said first liquid.

A specific object of this invention is to provide a novel ampoule having a barrier between the proximal and distal ends thereof so as to define a proximal compartment therein adjacent the proximal end of the ampoule and adapted to hold an acidified liquid local anaesthetic, and a distal compartment therein adjacent the distal end of the ampoule and adapted to hold an alkaline neutralizing reagent, with means to open an aperture in the barrier to permit the local anaesthetic and neutralizing reagent to mix during injection into the tissues of a patient.

Still another specific object of this invention is to provide an improved method for injecting an acidified liquid local anaesthetic through a body of alkaline neutralizing reagent into the tissues of a patient, whereby to mitigate or eliminate the pain usually associated with infiltration of acidified local anaesthetics.

Other and further objects of this invention will become apparent by reference to the accompanying specification, drawing and appended claims.

Briefly, the foregoing objects may be realized by providing an ampoule with a barrier between the distal and proximal ends thereof, which barrier divides the interior of the ampoule into a proximal compartment adjacent the proximal end of the ampoule and a distal compartment adjacent the distal end of the ampoule. The barrier has a portion adapted to be opened under pressure from the proximal compartment, whereby to place the proximal compartment in communication with the distal compartment. The proximal compartment is adapted to contain, from the perspective of a dental application, acidified liquid local anaesthetic, and the distal compartment is adapted to contain an alkaline neutralizing reagent in quantity and concentration sufficient to bring the pH of the combined liquids to 7.0 or above. The ampoule is adapted to fit in the barrel of a hypodermic syringe, the plunger of which, when advanced into the barrel, pressurizes the proximal compartment of the ampoule to open the said portion of the barrier and force the liquid local anaesthetic from the proximal compartment into the neutralizing reagent in the distal compartment and thence into the tissues of the patient.

DESCRIPTION OF THE DRAWING

Referring now to the drawing, in which like numerals represent like parts in the several views:

FIG. 1 represents a longitudinal medial section of the preferred embodiment of the ampoule of this invention.

FIG. 2 represents a longitudinal medial section, partially diagrammatic, of the preferred embodiment of the ampoule positioned in the barrel of a hypodermic syringe prior to injection.

FIG. 3 represents a longitudinal medial section, partially diagrammatic, of the preferred embodiment of the ampoule positioned in the barrel of a hypodermic syringe, the plunger of which has been advanced into the ampoule, to force the needle into the diaphragm at the distal end of the ampoule thereby to perforate the diaphragm, and to dislodge the plug from the aperture in the barrier thereby to place the two compartments of the aperture in communication with each other.

DESCRIPTION OF THE PREFERRED EMBODIMENT

Conventionally, ampoule 1 is an open tube, generally made of glass, with a proximal end 2 and a distal end 3. The tube is necked down at 4 and is provided with flange 5. Internally fitting rubber stopper 6 is positioned in the ampoule 1 at proximal end 2, thereby to seal the said proximal end 2. Rubber diaphragm 7 is held against flange 5 by centrally apertured cap 8 crimped about flange 5 and extending to contact reduced portion 4 of ampoule 1. In this manner, the distal end of ampoule 1 is sealed prior to use.

From the perspective of a dental infiltration, conventional ampoule 1 is filled with a sterile acidified liquid local anaesthetic. When the infiltration of the anaesthetic is to be performed, the ampoule 1 is placed in the barrel of a standard hypodermic syringe, the proximal end 2 of ampoule 1 facing the plunger of the syringe and the distal end 3 of ampoule 1 facing the proximal end of the hypodermic needle projecting into the barrel of the syringe. The ampoule 1 is then manually advanced in the barrel toward the distal end of the hypodermic syringe, thereby to cause the proximal end of the hypodermic needle to perforate rubber diaphragm 7 and communicate with the interior of ampoule 1. The distal end of the hypodermic needle is then inserted into the oral tissues of the patient, after which the dentist advances the plunger of the syringe, thereby forcing the rubber stopper 6 into the ampoule 1. As rubber stopper 6 is advanced into ampoule 1, it acts as a piston forcing the anaesthetic out of ampoule 1, through the hypodermic needle and into the oral tissues of the patient. As hereinbefore noted, the local anaesthetic is acidified, to increase its shelf life, and infiltration at a normal rate causes pain and discomfort to the patient.

In the preferred embodiment of the present invention, ampoule 1 is provided with barrier 9 having aperture 10 in which plug 11 is seated. Barrier 9 may be formed integrally with ampoule 1. Alternatively, barrier 9 may be formed separately and then securely sealed within ampoule 1 by suitable means such as a proper glass-to-glass cement if the ampoule 1 and barrier 9 are made of glass. Plug 11 is intended to securely close aperture 10 so as to prevent leakage of liquids therethrough prior to use. However, plug 11 is intended to be dislodged from aperture 10 under pressure from the proximal end 2 of ampoule 1 which pressure is low enough to avoid bursting of the said ampoule 1.

Barrier 9 divides the interior of ampoule 1 into two compartments, one of which is proximal compartment 12 adapted to hold acidified liquid local anaesthetic, such as lidocaine hydrochloride or mepivacaine hydrochloride and the other of which is distal compartment 13 adapted to hold sterile alkaline neutralizing reagent, such as aqueous solution of sodium bicarbonate.

The purpose of the alkaline neutralizing reagent is to neutralize the acidified liquid local anaesthetic and bring its pH to 7.0 or slightly above, preferably to 7.2–7.4, immediately prior to infiltrating the local anaesthetic into the oral tissues of the patient. The volume of distal compartment 13 and therefore of alkaline neutralizing reagent in distal compartment 13 will be substantially a function of the hydrogen ion concentration (actually the concentration of hydronium ion, $H_3O^+$) in the local anaesthetic and the alkalinity of the neutralizing reagent, and also of the desired final pH of the mixture of local anaesthetic and neutralizing reagent. Thus, the distance of barrier 9 from the distal end 3 of ampoule 1 will also be a function of the hydrogen ion concentration (actually, of the hydronium ion $H_3O^+$) of the acidified local anaesthetic and of the alkalinity of the neutralizing reagent, and also of the desired final pH of the mixture of local anaesthetic and neutralizing reagent.

In a typical situation, employing ampoule 1 of 1.8 ml. volume, wherein the local anaesthetic is 2% lidocaine hydrochloride and the neutralizing reagent is an aqueous solution containing 8.4% sodium bicarbonate, a desirable result is attained if the volume of the proximal compartment 12 is approximately 1.6 ml. and the volume of distal compartment 13 is approximately 0.2 ml. and barrier 9 is positioned accordingly between the proximal end 2 and the distal end 3 of ampoule 1.

In order to infiltrate local anaesthetic, by the method of the present invention, into the oral tissues of a patient, ampoule 1 is placed in the barrel of a conventional hypodermic syringe 14 in the same manner as a conventional ampoule. The proximal end 2 of ampoule 1 will face plunger 15 of the hypodermic syringe 14, and the distal end 3 of ampoule 1 will face the proximal end 16 of hypodermic needle 17, the said proximal end 16 of hypodermic needle 17 extending into the barrel of the hypodermic syringe 14. Plunger 15 of hypodermic syringe 14 conventionally has a barbed arrow adapted to positively engage rubber stopper 6 of ampoule 1. This barbed arrow is not shown because to do so would obfuscate FIGS. 2 and 3, and in any event is not necessary for an understanding of the invention. The operator (e.g., the dentist) will manually advance the ampoule 1 in the barrel of the syringe toward the distal end of the syringe to cause the proximal end 16 of the hypodermic needle 17 to perforate the rubber diaphragm 7 and communicate with distal compartment 13. The operator will then insert the distal end of hypodermic needle 17 into the oral tissues of the patient. Thereafter, the operator will advance plunger 15 against rubber stopper 6 at the proximal end 2 of ampoule 1, thereby forcing rubber stopper 6 into ampoule 1 and increasing the pressure within proximal compartment 12. This pressure will increase, with continued advancement of plunger 15, until plug 11 is dislodged from aperture 10 of barrier 9, whereupon proximal compartment 12 will communicate with distal compartment 13. Continued advancement of plunger 15 will force the acidified liquid local anaesthetic into the alkaline neutralizing reagent and the mixture of neutralized local anaesthetic and neutralizing reagent into the oral tissues of the patient, where it may be received without pain or discomfort even if introduced at a rate in excess of conventional very slow infiltration.

It will be seen that, after the ampoule 1 is loaded with sterile acidified liquid local anaesthetic and sterile alkaline neutralizing reagent, such sterility is not compromised by subsequent operations.

It will be seen further, that the local anaesthetic, being stored in acidified condition in the ampoule 1, will afford all of the benefits of extended shelf life.

It will also be seen that the acidified local anaesthetic may be conveniently neutralized, within ampoule 1, immediately prior to infiltration, in a most convenient manner and without waste.

The foregoing specification is illustrative of the principles of the invention. Since modifications and changes may readily occur to those skilled in the art to which this invention pertains, which modifications and changes will not depart from the spirit of the invention, such invention should not be considered as limited to the exact apparatus shown and described herein, and the appended claims should be construed as covering suitable modifications and equivalents.

I claim:

1. Ampoule comprising:
   (a) a tubular body having a proximal end and a distal end,
   (b) piston means sealing the proximal end of said tubular body,
   (c) diaphragm means sealing the distal end of said tubular body,
   (d) a barrier immovably mounted within said tubular body between the proximal and distal ends thereof,
   (e) said barrier and said piston means defining a first compartment within said tubular body,
   (f) said barrier and said diaphragm means defining a second compartment within said tubular body,
   (g) said barrier having a portion thereof adapted to be opened under pressure from said first compartment to place said first compartment in communication with said second compartment,
   (h) an acidified liquid in one of said compartments,
   (i) an alkaline liquid neutralizing reagent in the other of said compartments,
   (j) said last-mentioned compartment containing a volume of alkaline liquid neutralizing reagent sufficient to substantially neutralize said acidified liquid.

2. Ampoule comprising:
   (a) a tubular body having a proximal end and a distal end,
   (b) piston means sealing the proximal end of said tubular body,
   (c) diaphragm means sealing the distal end of said tubular body,
   (d) a barrier immovably mounted within said tubular body between the proximal and distal ends thereof,
   (e) said barrier and said piston means defining a first compartment within said tubular body,
   (f) said barrier and said diaphragm means defining a second compartment within said tubular body,
   (g) an aperture extending through said barrier in communicating relationship with said first and second compartments,
   (h) sealing means in sealing relationship with said aperture and preventing communication therethrough between said first and second compartments,
   (i) said sealing means being adapted to be removed from sealing relationship with said aperture upon an increase in pressure from said first compartment thereby to place said first compartment in communication with said second compartment,
   (j) an acidified liquid in one of said compartments,
   (k) an alkaline liquid neutralizing reagent in the other of said compartments,
   (l) said last-mentioned compartment containing a volume of alkaline liquid neutralizing reagent sufficient to substantially neutralize said acidified liquid.

3. Ampoule for medical use, said ampoule comprising:
   (a) a tubular body having a distal end and a proximal end, (b) a barrier immovably transversely mounted within said tubular body between the proximal and distal ends thereof,
(c) a rubber piston slidably mounted within said tubular body adjacent the proximal end thereof,
(d) a first compartment within said tubular body defined by said barrier and said rubber piston,
(e) a rubber diaphragm secured to and sealing the distal end of said tubular body, said rubber diaphragm being adapted to be perforated to provide a hole extending therethrough,
(f) a second compartment within said tubular body defined by said barrier and said rubber diaphragm,
(g) said barrier having an aperture extending therethrough in communicating relationship with said first and second compartments,
(h) a rubber plug seated in said aperture of said barrier and adapted to prevent leakage therethrough,
(i) an acidified liquid local anaesthetic in one of said compartments,
(j) an alkaline liquid neutralizing reagent in the other of said compartments,
(k) said last-mentioned compartment containing a volume of alkaline liquid neutralizing reagent sufficient to substantially neutralize said acidified liquid local anaesthetic,
(l) said rubber piston being adapted to be advanced toward said barrier to pressurize said first compartment thereby to dislodge said rubber plug from said aperture into said distal compartment and thereafter to force the liquid in said first compartment into said second compartment and to force substantially neutralized liquid local anaesthetic out of said tubular body through said hole in said diaphragm.

* * * * *